United States Patent [19]

Spillert et al.

[11] Patent Number: 4,833,132

[45] Date of Patent: May 23, 1989

[54] PROCESS FOR TREATING A WARM-BLOODED ANIMAL WITH AN ANTINEOPLASTIC/ANTIME-TASTATIC EFFECTIVE COMPOSITION

[75] Inventors: Charles R. Spillert, West Orange, N.J.; Corinne Devereux, Bronxville, N.Y.; Eric J. Lazaro, Jersey City, N.J.

[73] Assignee: University of Medicine and Dentistry of New Jersey, Newark, N.J.

[21] Appl. No.: 30,283

[22] Filed: Mar. 23, 1987

Related U.S. Application Data

[63] Continuation of Ser. No. 655,144, Sep. 27, 1984, abandoned.

[51] Int. Cl.$^4$ .................. A61K 31/635; A61K 31/505
[52] U.S. Cl. ..................................... 514/158; 514/275
[58] Field of Search .............................. 514/158, 275

[56] References Cited

PUBLICATIONS

Chemical Abstracts 77:56537n (1972).

*Primary Examiner*—Jerome D. Goldberg
*Attorney, Agent, or Firm*—Weiser & Stapler

[57] ABSTRACT

There is disclosed a process for treating a warm-blooded animal wherein there is administered to the warm-blooded animal a therapeutically effective amount of composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof. The composition is useful to treat a fibrosarcoma ($SAD_2$) tumor in warm-blooded animals.

17 Claims, No Drawings

PROCESS FOR TREATING A WARM-BLOODED ANIMAL WITH AN ANTINEOPLASTIC/ANTIME-TASTATIC EFFECTIVE COMPOSITION

This application is a continuation of U.S. patent Ser. No. 655,144, filed 9/27/84, now abandoned.

FIELD OF THE INVENTION

This invention relates to antineoplastic/antimetatstatic effective compositions, and more particularly to a process for treating a warm-blooded animal with a therapeutically effective amount of a composition effective to treat a fibrosarcoma (SAD$_2$) tumor.

BACKGROUND OF THE INVENTION

In U.S. Pat. No. 2,909,522, there is disclosed 2,4-diamino-5-(3,4,5-trimethoxybenzyl) pyrimidine and a process for preparing same. In U.S. Pat. No. 2,888,455, there is disclosed 5-methyl-3-sulfanilamidosoxazole and a process for preparing same. In U.S. Pat. No. Re. 28,636 there is disclosed a therapeutically active antibacterial composition comprising 5-methyl-3-sulfanilamidoisoxazole, or a salt thereof together with a pharmaceutically acceptable base and 2,4-diamino-5-(3,4,5-trimethoxybenzyl) pyrimidine or a salt thereof with a pharmaceutically acceptable acid.

SUMMARY OF THE INVENTION

To a warm-blooded animal there is administered a therapeutically effective amount of composition effective to treat a fibrosarcoma (SAD$_2$) tumor selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof.

DETAILED DESCRIPTION OF THE INVENTION

It has been surprisingly found that beneficial effects in neoplasia result by administering to a warm-blooded animal a therapeutically effective amount to control a fibrosarcoma (SAD$_2$) tumor of a composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrmidine with a pharmaceutically acceptable acid and mixtures thereof.

In a most comprehensive embodiment, the present invention relates to a pharmaceutical composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof, useful in the treatment of a warm-blooded animal for effects thereof.

In a more particular embodiment, the present invention relates to a pharmaceutical composition, in suitable intravenous or oral dosage forms, which composition is selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof, useful in the treatment of a warm-blooded animal for treating a fibrosarcoma (SAD$_2$) tumor.

The expression "salts thereof with pharmaceutically acceptable bases" utilized throughout the present specification to denote salts of 5-methyl-3-sulfanilamidoisoxazole, preferably includes those formed utilizing an alkali metal base, such as sodium hydroxide, potassium hydroxide, etc.

The expression "salts thereof with pharmaceutically acceptable acids" utilized throughout the present specification to denote salts of 2,4-diamino-5-(3,4,5-trimethoxybenzyl) pyrimidine, preferably includes those formed utilizing mineral acids, such as hydrochloric acid, sulfuric acid, etc.; and organic acids, such as acetic acid, citric acid, lactic acid, maleic acid, salicylic acid, etc.

It is also within the scope of this invention to administer each active component individually. Thus, it is possible to formulate each of the components into separate dosage forms in accordance with procedures hereinbefore and hereinafter described for the combination.

The compositions of this invention are prepared simply by admixing 5-methyl-3-sulfanilamidoisoxazole or a salt thereof with a pharmaceutically acceptable base and 2,4-diamino-5-(3,4,5-trimethoxybenzyl) pyrimidine or a salt thereof with pharmaceutically acceptable acid.

In addition to the therapeutically active ingredients mentioned heretofore, the compositions of this invention can contain, as optional ingredients, any of the various adjuvants which are used ordinarily in the production of pharmaceutical preparations. Thus, for example, in formulating the present compositions into the desired intravenous form, one may use, as optional ingredients, antiplatelets such as aspirin, prostaglandins ($E_1$ and $I_2$), chemotherapeutic agents such as methotrexate, vincristine, cis-platinum, and anticoagulants such as warfarin. It should be fully understood, however, that the optional ingredients herein named are given by way of example only and that the invention is not restricted to the use hereof. On the contrary, other such adjuvants, the identity and use of which are well known in the art, can be, and are, employed in carrying out this invention.

The ratios in which the therapeutically active components are utilized in the compositions of this invention can be varied within wide limits. For example, the compositions can contain from about 1 to about 30 parts of 5-methyl-3-sulfanilamidoisoxazole or an equivalent amount of salt thereof to about 30 to about 1 part of 2,4-diamino-5-(3,4,5-trimethoxybenzyl) pyrimidine or an equivalent amount of salt thereof, preferably from about 5 to about 15 parts of 5-methyl-3-sulfanilamidoisoxazole or an equivalent amount of a salt thereof to one part of 2,4-diamino-5-(3,4,5-trimethoxybenzyl) pyrimidine or an equivalent amount of salt thereof.

The composition of the present invention can be administered in unit dosage forms which contain 500 mg. of 5-methyl-3-sulfanilamidoisoxazole or an equivalent amount of a salt thereof and from about 25 mg. to about 100 mg. of 2,4-diamino-5-(3,4,5-trimethoxybenzyl) pyrimidine or an equivalent amount of a salt thereof. However, it is also within the scope of this invention to utilize a unit dosage form which will contain from about 250 mg. to about 800 mg. of 5-methyl-3-sulfanilamidoisoxazole or an equivalent amount of a salt thereof and from about 12.5 mg. to about 160 mg. of 2,4-diamino-5-(3,4,5-trimethoxybenzyl) pyrimidine or an equivalent amount of a salt thereof. The frequency with which any such unit dosage form will be administered to a warm-blooded animal will vary, depending upon the quantity of medicament present therein and the needs and requirements of the warm-blooded animal. Under ordinary circumstances, however, about a total of 60 mg./kg. of 5-methyl-3-sulfanilamidoisoxazole and about a total of 8 mg./kg. of 2,4-diamino-5-(3,4,5-trimethoxybenzyl) pyrimidine, in combination, can be administered daily in several doses.

As hereinabove discussed, detailed description is made with reference to unit dosages whether in intravenous or oral form, the frequency and dosage levels are best related with regard to the effectiveness in treating a fibrosarcoma (SAD$_2$) tumor in terms of component levels in the plasma of the warm-blooded animals being treated of the composition selected from the group consisting of 5-methyl-3-sulfanilamidoisoxazole, a salt of 5-methyl-3-sulfanilamidoisoxazole with a pharmaceutically acceptable base, 2,4-diamino-5-(3,4,5-trimethoxybenzyl) pyrimidine, a salt of 2,4-diamino-5-(3,4,5-trimethoxybenzyl) pyrimidine with a pharmaceutically acceptable acid and mixtures thereof. Generally, it is preferably desired to maintaini in the plasma of the warm-blooded animal a component level of the 5-methyl-3-sulfanilamidoisoxazole or an equivalent amount of the salt thereof of from about 80 to 160, preferably about 110 μg./cc. and/or a component level of the 2,4-diamino-5-(3,4,5-trimethoxybenzyl) pyrimidine or an equivalent amount of the salt thereof of from about 5 to 15, preferably 10 μg./cc.

This invention relates to the invention described in copending applications (Ser. Nos. 655,079; 655,227; 655,145; and 655,080; now U.S. Pat. Nos. 4,632,920; 4,698,335; 4,632,919; and 4,661,478, respectively filed on even date herewith, the teachings of which are incorporated) by reference herein.

The foregoing, notwithstanding, it should be fully understood that the dosages set forth herein are exemplary only and they do not, to any extent, limit the scope or practice of the present invention. As indicated hereinbefore, the combination of this invention has unexpectedly been found to be particularly useful for its effects in the treatment of a fibrosarcoma (SAD$_2$) tumor in warm-blooded animals.

The invention will be understood better by reference to the following examples which are given for illustration purposes and are not meant to limit the invention.

EXAMPLES

CDF$_1$ mice (23 +2 gm.) were implanted with a fibrosarcoma (SAD$_2$) subcutaneously. One week later all mice received pentobarbital sodium anesthesia followed by either 0.1 cc. Injectable Composition (Trimethoprim 16 mg./cc., Sulfamethoxazole 80 mg./cc., Dosage: 320 mg./kgS, 64 mg./kgT) or an equal volume of saline. One hour later all mice received 400 rads (8MeV Photon) to the tumor.

TABLE

| | Two Week Survivals | | |
|---|---|---|---|
| Saline | 2/20 | 20% | $p < .05$ |

TABLE-continued

| | Two Week Survivals | |
|---|---|---|
| I.C. | 5/11 | 46% |

The two week survival time of recipients of the Injectable Composition was significantly greater than that of the control and suggest beneficial effects in neoplasia of such Injectable Composition.

Numerous modifications and variations of the present invention are possible in light of the above teachings and, therefore, within the scope of the appended claims, the invention may be practiced otherwise than as particularly described.

What is claimed:

1. A process for treating a warm-blooded animal having a fibrosarcoma (SAD$_2$) tumor which comprises administering to said animal
   (a) 400 rads of radiation,
   (b) from about 1 to about 30 parts selected from the group of 5-methyl-3-sulfanilamidoisoxazole and a alkali metal salt of 5-methyl-3-sulfanilamidosoxazole with a pharmaceutically acceptable base and,
   (c) from about 30 to about 1 part selected from the group of 2, 4-diamino-5-(3,4,5-trimethoxybenzyl) pyrimidine and a salt of 2,4-diamino-5-(3,4,5-trimethoxybenzyl) pyrimidine with a pharmaceutically acceptable acid,
   said compounds (b) and (c) being administered in an amount effective to lengthen the survival of said animal having a tumor.

2. The process as defined in claim 1 wherein the effective amount of the compounds administered comprise from about 250 mg to about 800 mg of 5-methyl-3-sulfanilamidoisoxazole or an alkali metal salt thereof with a pharmaceutically acceptable base and from about 12.5 mg. to about 160 mg. of 2,4-di-amino-5 (3,4,5-trimethoxy benzyl) pyrimidine or a salt thereof with a pharmaceutically acceptable acid.

3. The process of claim 1 wherein the compounds are administered intravenously.

4. The process of claim 1 wherein the compounds are administered orally.

5. The process of claim 1 wherein the pharmaceutically acceptable base with which the alkali metal salt of 5-methyl-3-sulfanilamidoisoxazole is formed is selected from the group consisting of sodium hydroxide and potassium hydroxide.

6. The process of claim 1 wherein the pharmaceutically acceptable acid with which the salt of 2,4-diamino-5-(3,4,5-trimethoxybenzyl) pyrimidine is formed is a mineral acid or an organic acid.

7. The process of claim 6 wherein the mineral acid is selected from the group consisting of hydrochloric acid and sulfuric acid.

8. The process of claim 6 wherein the organic acid is selected from the group consisting of acetic acid, citric acid, lactic acid, maleic acid and salicyclic acid.

9. The process of claim 1 wherein the compounds are administered individually.

10. The process of claim 1 wherein the ratio of the amount administered of 5-methyl-3-sulfanilamidoisoxazole or an equivalent salt and the amount administered of 2,4-diamino-5-(3,4,5-trimethoxybenzyl) pyrimidine is between about 5 and about 15 to 1.

11. The process of administering the compounds of claim 1 wherein up to about 160 mg/kg of 5-methyl-3- sulfanilamidoisoxazole and up to about 8 mg/kg of 2,4-diamino-5-(3,4,5-trimethoxybenzyl) pyrimidine are administered daily to said warm-blooded animal.

12. The process of claim 11 wherein the daily administration of the compounds is in several doses.

13. The process of claim 1 wherein the radiation is administered subsequent to the administration of the compounds.

14. A therapeutic method for treatment of a fibrosarcoma (SAD$_2$) tumor in a warm-blooded animal which comprises periodically administering to said warm-blooded animal 400 rads of radiation and a therapeutic composition which comprises a therapeutically effective amount of an antineoplastic/antimetastatic compound selected from the group consisting of 5-methyl-3-sulfanilamidoisoxazole or an alkali metal salt thereof with a pharmaceutically acceptable base sufficient to maintain a blood plasma concentration of said compound between about 80 and about 160 micrograms/cc.

15. The process as defined in claim 14 wherein a composition concentration is maintained at about 110 $\mu$g./cc.

16. A therapeutic method for treatment of a fibrosarcoma (SAD$_2$) tumor in a warm-blooded animal which comprises periodically administering to said warm-blooded animal 400 rads of radiation and a therapeutically effected amount of an antineoplastic/antimetastatic composition selected from the group consisting of 2,4-diamino-5-(3,4,5-trimethoxybenzyl) pyrimidine or a salt thereof with a pharmaceutically acceptable acid sufficient to maintain a blood plasma concentration of said compound between about 5 and about 15 micrograms/cc.

17. The process as defined in claim 16 wherein a composition concentration is maintained at about 10 $\mu$g./cc.

* * * * *